United States Patent [19]

Denzel et al.

[11] 3,996,233
[45] Dec. 7, 1976

[54] AMINO DERIVATIVES OF IMIDAZO[4,5-b]PYRIDINES

[75] Inventors: Theodor Denzel, Regensburg; Hans Hoehn, Tegernheim, both of Germany

[73] Assignee: E. R. Squibb & Sons, Inc., Princeton, N.J.

[22] Filed: Feb. 10, 1975

[21] Appl. No.: 548,325

[52] U.S. Cl. .................. 260/295.5 B; 260/294.8 C
[51] Int. Cl.² .............. C07D 401/04; C07D 471/02
[58] Field of Search ............ 260/295.5 B, 294.8 C

[56] References Cited
UNITED STATES PATENTS 3,828,057  8/1974  Denzel et al. ............... 260/295.5 B
3,891,660  6/1975  Denzel et al. ............... 260/295.5 B

*Primary Examiner*—Sam Rosen
*Attorney, Agent, or Firm*—Lawrence S. Levinson; Merle J. Smith

[57] ABSTRACT

Amino derivatives of imidazo[4,5-b]pyridines having the general formula:

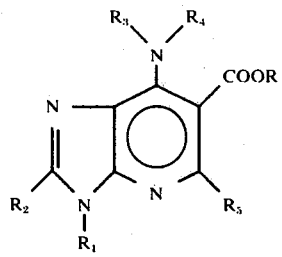

are disclosed. The novel compounds are useful as central nervous system depressants and antiinflammatory agents. In addition, the new compounds increase the intracellular concentration of adenosine 3',5'-cyclic-monophosphate.

17 Claims, No Drawings

AMINO DERIVATIVES OF IMIDAZO[4,5b]PYRIDINES

SUMMARY OF THE INVENTION

This invention relates to new amino derivatives of imidazo [4,5-b]pyridines and salts of these compounds as well as the process for producing them. These new compounds have the formula

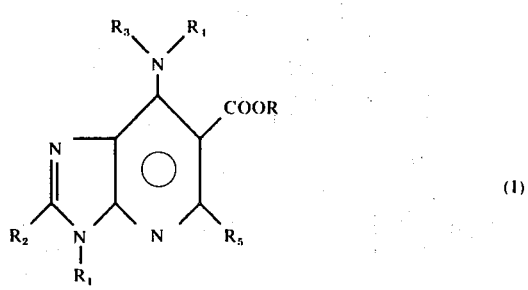

The symbols have the following meanings in formula I and throughout this specification. R is hydrogen or lower alkyl. $R_1$ is hydrogen, lower alkyl, phenyl, phenyl-lower alkyl, cyclo-lower alkyl, lower alkanoyl, benzoyl or substituted benzoyl.

$R_2$ is hydrogen, lower alkyl, phenyl-lower alkyl or hydroxy.

The basic nitrogen group

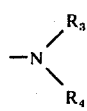

is an acyclic amino group wherein $R_3$ and $R_4$ each is hydrogen, lower alkyl, lower alkenyl, lower alkanoyl, phenyl, substituted phenyl (i.e., the phenyl ring contains one or two simple substituents including lower alkyl, halogen, trifluoromethyl, amino or carboxy, preferably only one of the last three substituents), phenyl-lower alkyl, di-lower alkylamino-lower alkyl, benzoyl, substituted benzoyl, lower alkanesulfonyl, benzenesulfonyl or substituted benzenesulfonyl. The substituents on the phenyl groups of the substituted aromatic radicals are the same as above (preferably only one of the last groups as above). This basic group may also form a heterocyclic of 5- or 6-members in which an additional nitrogen is present, i.e., the pyrrolidino, piperidino, pyrazolyl, pyrimidinyl, pyridazinyl or piperazinyl radicals, each of which may also bear as a substituent a hydroxy-lower alkyl group, a phenyl group or one or two lower alkyl groups. That is to say, $R_3$ and $R_4$ each is hydrogen, lower alkyl, $R_6$, $R_7$-phenyl (wherein $R_6$ and $R_7$ each is hydrogen, halogen, lower alkyl, amino, trifluoromethyl or carboxy), phenyl-lower alkyl, $R_6$, $R_7$-phenyl-lower alkyl, di-lower alkylamino-lower alkyl, benzoyl, $R_6$, $R_7$-benzoyl, phenyl-lower alkanoyl, $R_6$, $R_7$-phenyl-lower alkanoyl, lower alkylsulfonyl, benzenesulfonyl, $R_6$, $R_7$-benzenesulfonyl or $R_3$ and $R_4$ together with the nitrogen to which they are attached form one of the heterocyclics mentioned above or the $R_8$-monosubstituted or $R_8$, $R_9$-disubstituted derivative (wherein $R_8$ and $R_9$ each is lower alkyl, phenyl or hydroxy-lower alkyl). $R_5$ is hydrogen, lower alkyl, phenyl or substituted phenyl (in which the phenyl substituents are $R_6$ or $R_7$ as above).

The lower alkyl groups in any of the foregoing radicals are straight or branched chain hydrocarbon groups of up to seven carbon atoms from methyl to heptyl, like methyl, ethyl, propyl, isopropyl, butyl, t-butyl and the like. The lower alkenyl groups are similar groups with one double bond. In each instance, the $C_1$ to $C_4$ groups are preferred, especially the one and two carbon members of the series. The cycloalkyl groups are the three to seven carbon alicyclics from cyclopropyl to cycloheptyl, cyclopentyl and cyclohexyl being preferred, especially the latter.

All four of the common halogens are contemplated but chlorine and bromine are preferred.

The lower alkanoyl groups either alone or in conjunction with another radical like the phenyl radical include the acyl groups of the lower fatty acids, like acetyl, propionyl, isopropionyl, butyryl, etc., preferably those with up to four carbons and especially acetyl and propionyl.

The products of the examples, which are representative of the various compounds of this invention and serve as models for the preparation of additonal products of this invention, constitute preferred embodiments.

Preferred members of each group are as follows:
R is hydrogen or lower alkyl, especially $C_1$–$C_4$ alkyl.
$R_1$ is hydrogen, lower alkyl (especially $C_1$–$C_4$ alkyl), phenyl, phenyl-lower alkyl (especially benzyl and phenethyl) and lower alkanoyl (especially acetyl and propionyl). Especially preferred in this group are ethyl, benzyl and phenethyl.

$R_2$ is hydrogen, hydroxy, lower alkyl (especially $C_1$–$C_4$ alkyl) or phenyl-lower alkyl (especially benzyl and phenethyl).

$R_3$ and $R_4$ each is hydrogen or lower alkyl (especially $C_1$–$C_4$ alkyl).

$R_5$ is hydrogen, $C_1$–$C_3$ alkyl or phenyl, especially hydrogen, methyl and ethyl.

Especially preferred compounds are those wherein R and $R_1$ each is hydrogen or ethyl, $R_2$ is hydrogen, methyl or hydroxy, $R_3$ is hydrogen, $R_4$ is lower alkyl, particularly $C_1$–$C_4$ alkyl, and $R_5$ is lower alkyl, particularly methyl.

DETAILED DESCRIPTION

The new compounds of formula I are formed by the following series of reactions.

A 4,6-dihydroxypyridine carboxylic acid ester of the formula

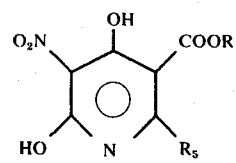

[produced analogous to the procedure described in Chem. Ber. 99, page 244, (1966)], is made to react with an inorganic acid chloride like phosphorus oxychloride, producing a compound of the formula

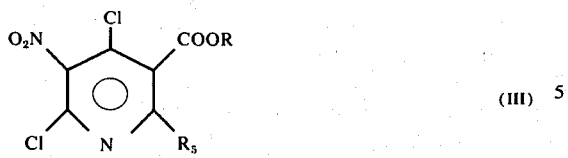

(III)

with the two chlorine atoms in the 4,6-position of the molecule. Compounds of formula I wherein $R_3$ is hydrogen are produced by treating a compound of formula III in a solvent like alcohol with the appropriate amine of the formula

(IV)

at about 80° C. in the presence of a base like triethylamine. By this reaction a product of the formula

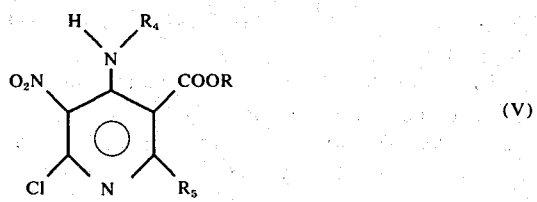

(V)

is obtained.

Treatment of the compound of formula V with an appropriate amine of the formula

(VI)

in the presence of a base like triethylamine produces a compound of the formula

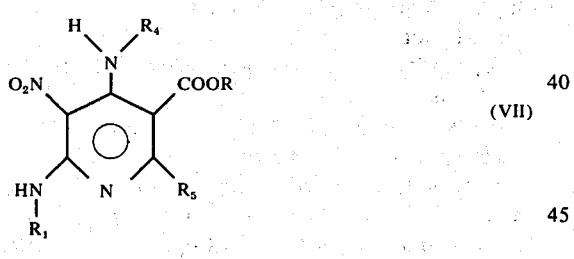

(VII)

which is then hydrogenated catalytically with a catalyst like palladium or nickel or by reduction with a metal-acid pair of zinc in acetic acid, iron in hydrochloric acid or the like, producing a tri-amino compound of the formula

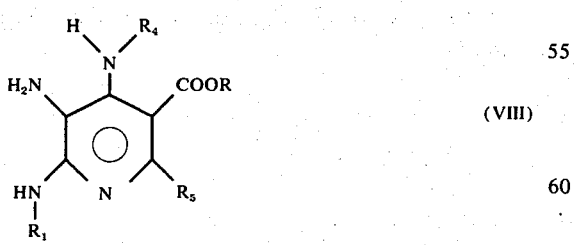

(VIII)

Compounds of formula VIII, wherein $R_3$ is other than hydrogen are produced by the following alternate route:

The dichloro compound of formula III is made to react with an alkyl benzylamine of the formula

(IX)

producing a compound of the formula

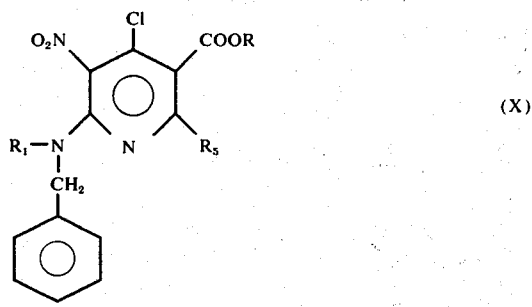

(X)

which is now treated with the appropriate amine of the formula

(XI)

By this reaction a compound of the formula

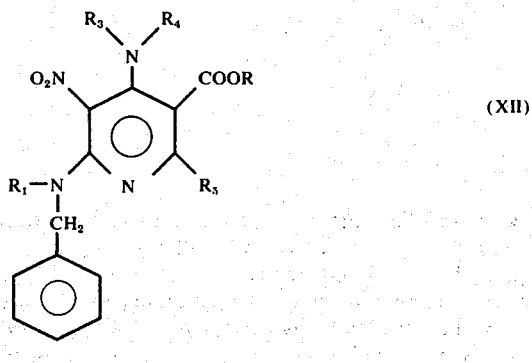

(XII)

is formed.

Hydrogenation of the compound of formula XII in the presence of a catalyst like palladium or nickel yields the product of formula VIII, wherein the nitrogen in the 4-position is disubstituted (i.e., $R_3$ and $R_4$ are both other than hydrogen).

Products of formula I can now be obtained by reacting the compound of formula VIII with the appropriate carbonic acid or carbonic ortho ester of the formula

(XIII)

In the case where $R_3$ is hydrogen, sometimes mixtures with the imidazo [4,5-c]pyridine of the formula

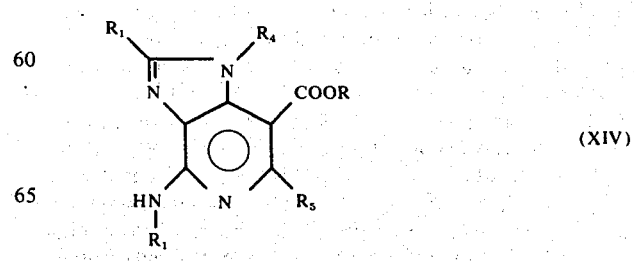

(XIV)

are obtained. Separation is easily accomplished by recrystallization.

Compounds of formula I can also be produced by a modification of the foregoing procedure.

The 4,6-dichloro compound of formula III is made to react with an alkylhydrazine of the formula

$$R_1-NH-NH_2 \quad (XV)$$

This reaction gives rise to the formation of a compound of the formula

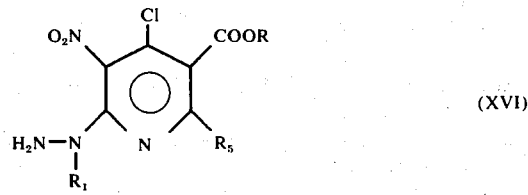

(XVI)

which is hydrogenated in the presence of Raney-nickel to give a compound of the formula

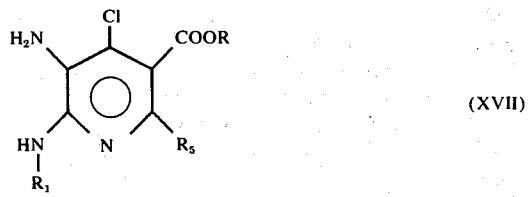

(XVII)

Treatment of this compound with the ortho carbonic ester of formula XIII results in the formation of a compound of the formula

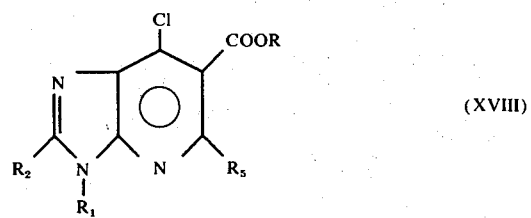

(XVIII)

with a chlorine atom in the 4-position of the molecule.

The compound of formula I is now obtained by reaction of the compound of formula XVIII with the appropriate amine of formula XI or formula IV.

Compounds of formula I, wherein $R_2$ is hydroxy, are produced by another modification of the foregoing procedure.

A compound of formula VIII is made to react with a chloroformic acid ester which produces a compound of the formula

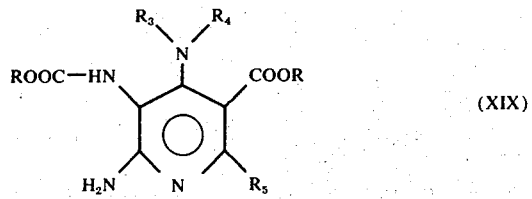

(XIX)

The compound of formula I wherein $R_2$ is hydroxy, is now produced by cyclization of the compound of formula XIX by heating at about 150°–200° C.

The compounds of formula I form salts which are also part of this invention. The salts include acid addition salts, particularly the non-toxic, physiologically acceptable members. The bases of formula I form salts by reaction with a variety of inorganic or organic acids providing acid addition salts including, for example, hydrohalides (especially hydrochloride and hydrobromide), sulfate, nitrate, borate, phosphate, oxalate, tartrate, malate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts can then be formed from the free base by reaction with an equivalent of acid.

The new compounds of this invention are central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-tonic, physiologically acceptable acid addition salt thereof, is administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. These may be conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The new compounds also increase the intracellular concentration of adenosine-3',5'-cyclic monophosphate, and thus by the administration of about 1 to 100 mg/kg/day, preferably about 10 to 50 mg/kg, in single or two or four divided doses in conventional oral or parenteral dosage forms such as those described above may be used to alleviate the symptoms of asthma.

The new compounds of this invention, in addition, have antiinflammatory properties and are useful as anti-inflammatory agents, for example, to reduce local inflammatory conditions such as those of an edematous nature or resulting from proliferation of connective tissue in various mammalian species such as rats, dogs or the like when given orally in dosages of about 5 to 50 mg/kg/day, preferably 5 to 25 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream can also be used.

The following examples are illustrative of the invention. All temperatures are in degrees celsius.

EXAMPLE 1

7-[[3-Dimethylamino)propyl]amino]-3-ethyl-2,5-dimethyl-3H-imidazo[4,5-b]pyridine-6-carboxylic acid, ethyl ester a. 4,6-Dichloro-2-methyl-5-nitropyridine-3-carboxylic acid ethyl ester 242 g. of 4,6-dihydroxy-2-methyl-5-nitropyridine-3-carboxylic acid ethyl ester (1 Mol.) are heated at 120° with 500 ml. of phosphorus oxychloride for 3 hours. After this time, the excess phosphorus oxychloride is removed in vacuo and the black residue is decomposed by pouring into ice-water. About 1 liter of chloroform is added and the mixture is filtered to remove undissolved material. The organic layer is separated and the aqueous phase extracted twice with 100 ml. portions of chloroform. The extract is dried over calcium chloride, filtered and evaporated to dryness. The resulting oil is crystallized with about 500 ml. of petroleum ether yielding 153 g. of 4,6-dichloro-2-methyl-5-nitropyridine-3-carboxylic acid ethyl ester (55%), m.p. 45°–46°.

b. 6-Chloro-4-[[3-(dimethylamino)propyl]amino]-2-methyl-5-nitropyridine-3-carboxylic acid, ethyl ester 139.5 g. of 4,6-dichloro-2-methyl-5-nitropyridine-3-carboxylic acid ethyl ester (0.5 Mol.) in 500 ml. of ethyl alcohol are heated at reflux temperature. 60 g. of triethylamine are added and then 51 g. of 3-(dimethylamino)propylamine are slowly dropped in with stirring. After the addition is completed, heating is continued for 10 minutes. The solvent is distilled off and the residue is treated with 200 ml. of water and made alkaline (pH 9–10) with sodium hydroxide. The mixture is extracted three times with 150 ml. portions of ether. The organic layers are combined, dried over calcium chloride and evaporated to dryness. The residue is recrystallized from methanol, yield 110 g. (64%), m.p. < 20°.

c. 4-[[3-(Dimethylamino)propyl]amino]-6-ethylamino-2-methyl-5-nitropyridine-3-carboxylic acid ethyl ester 34.5 g. of 6-chloro-4-[[3-(dimethylamino)propyl]amino]-2-methyl-5-nitropyridine-3-carboxylic acid ethyl ester (0.1 Mol.) are dissolved in 200 ml. of methanol. A mixture of 15 g. of triethylamine and 6 g. of ethylamine are added and the solution is refluxed for one hour with stirring. The solvent is distilled off in vacuo and the residue treated with about 100 ml. of water. The aqueous phase is extracted three times with 100 ml. portions of ether, the ether layers are combined, dried over calcium chloride and the solvent distilled off. The resulting yellow oil is recrystallized from ether/ligroin, yield 31 g. (88%), m.p. < 20°.

d. 5-Amino-4-[[3-(dimethylamino)propyl]amino]-6-ethyl-5-amino-2-methylpyridine-3-carboxylic acid ethyl ester 7 g. of 4-[[3-(dimethylamino)propyl]amino]-6-ethyl-amino-2-methyl-5-nitropyridine-3-carboxylic acid ethyl ester (0.02 Mol.) are dissolved in butyl alcohol and hydrogenated in the presence of palladium on charcoal catalyst at about 80° and 3 atm. of hydrogen pressure. When the theoretical amount of hydrogen has been absorbed, the catalyst is filtered off and the solvent removed in vacuo. The oily residue is distilled under reduced pressure, yield 6 g. (94%), b.p.$_{0.01}$ 190°–200°.

e. 7-[[(3-Dimethylamino)propyl]amino]-3-ethyl-2,5-dimethyl-3H-imidazo[4,5-b]pyridine-6carboxylic acid ethyl ester 6.4 g. of 5-amino-4-[[3-(dimethylamino)propyl]amino]-6-ethyl-5-amino-2-methylpyridine-3-carboxylic acid ethyl ester (0.02 Mol.) are refluxed in 50 ml. of acetic acid for 48 hours. The excess acetic acid is removed in vacuo and the residue distilled under reduced pressure, b.p.$_{0.05}$ 210°–220°, m.p. 68°–70° (ether), yield 5 g. (72%).

EXAMPLE 2

7-(Butylamino)-3-ethyl-2,5-dimethyl-3H-imidazo[4,5-b]pyridine-6-carboxylic acid, ethyl ester hydrate (1:1)

a. 4-Butylamino-6-chloro-2methyl-5nitropyridine-3-carboxylic acid ethyl ester 139.5 g. of 4,6-dichloro-2-methyl-5-nitropyridine-3-carboxylic acid ethyl ester (0.5 Mol.) are dissolved in about 500 ml. of methanol. 60 g. of triethylamine are added and the solution is heated at reflux temperature. At this point, 36.5 g. of n-butylamine are added dropwise. The solvent is then removed in vacuo and 500 ml. of benzene are added to the residue. The triethylamine hydrochloride is filtered off and the solvent evaporated. The resulting oil is dissolved in 300 ml. of methanol and yields on cooling 110 g. of 4-butylamino-6-chloro-2-methyl-2-nitropyridine-3-carboxylic acid, ethyl ester (70%), m.p. 33°–35° (methanol).

b. 4-Butylamino-6-ethylamino-2-methyl-5-nitropyridine-3-carboxylic acid, ethyl ester 4-Butylamino-6-chloro-2-methyl-5-nitropyridine-3-carboxylic acid ethyl ester is treated with ethylamine according to the procedure in Example 1 c and 4-butylamino-6-ethylamino-2methyl-5-nitropyridine-3-carboxylic acid ethyl ester is obtained, yield 86%, m.p. 53°–55° (methanol).

c. 5-Amino-4-butylamino-6-ethylamino-2-methylpyridine-3-carboxylic acid, ethyl ester 4-Butylamino-6-ethylamino-2-methyl-5-nitropyridine-3-carboxylic acid ethyl ester is hydrogenated according to the procedure of Example 1 d and 5-amino-4-butylamino-6-ethylamino-2-methylpyridine-3-carboxylic acid ethyl ester results, yield 89%, b.p. $_{0.05}$ 190°–200°.

d. 7-(Butylamino)-3-ethyl-2,5-dimethyl-3H-imidazo[4,5-b]pyridine-6-carboxylic acid, ethyl ester, hydrate (1:1)

5.8 g. of 5-amino-4-butylamino-6-ethylamino-2-methylpyridine-3-carboxylic acid, ethyl ester and 20 ml. of acetic acid trimethyl ester are refluxed for 12 hours with stirring. The excess orthoester is removed in vacuo and the resulting oil recrystallized from petroleum ether. The recrystallization step is repeated three times in order to remove all impurities, yield 4.1 g. (62%), m.p. 73°–74°.

The following additional compounds are prepared by the procedure of Example 2: 7-butylamino-5-methyl-3H-imidazo[4,5-b]pyridine-6-carboxylic acid, ethyl ester, m.p. 120°–122°, and 7-butylamino-2,5-dimethyl-3H-imidazo[4,5-b]-pyridine-6-carboxylic acid ethyl ester, m.p. 148°–149°.

EXAMPLE 3

3-Ethyl-5-methyl-7-(4-methyl-1-piperazinyl)-3H-imidazo[4,5-b]-pyridine-6-carboxylic acid, ethyl ester a. 4-Chloro-6-[ethyl(phenylmethyl)amino]-2-methyl-5-nitro-3-pyridine carboxylic acid, ethyl ester 279 g. of 4,6-dichloro-2-methyl-5-nitropyridine-3-carboxylic acid ethyl ester are dissolved in 700 ml. of alcohol. 150 g. of triethylamine are added and at reflux temperature 135 g. of benzyl(ethyl)amine are slowly dropped in. After the addition is completed, the heating is continued for another hour. After this time, the solvent is removed in vacuo, 300 ml. of water are added and the mixture extracted three times with 200 ml. portions of ether. The organic layers are combined, dried with calcium chloride and the solvent is distilled off. The resulting oil is distilled in vacuo, b.p.$_{0.05}$ 210°–220°. The crude product is dissolved in 300 ml. of ether and cooled to about −50°. After 24 hours, the isomeric compound 6-chloro-4-[ethyl(phenylmethyl)amino]-2-methyl-5-nitro-3-pyridinecarboxylic acid ethyl ester precipitates, is filtered off and the filtrate evaporated to dryness. The resulting 4-chloro-6-[ethyl(phenylmethyl)amino]-2-methyl-5-nitro-3-pyridinecarboxylic acid, yield 215 g. (56%) is used without further purification.

b. 6-[Ethyl(phenylmethyl)amino]-2-methyl-4-(4-methyl-1piperazinyl)-5-nitropyridine-3-carboxylic acid, ethyl ester 37.8 g. of 4-chloro-6-[ethyl(phenylmethyl)amino]-2-methyl-5-nitro-3-pyridinecarboxylic acid ethyl ester (0.1 Mol.), 12 g. of N-methylpiperazine (0.12 Mol.) and 15 g. of triethylamine (0.15 Mol.) are refluxed in 200 ml. of ethanol for three hours. After this time, the solvent is distilled off, the residue is dissolved in 100 ml. of water, made alkaline with potassium hydroxide and extracted three times with 100 ml. portions of ethyl acetate. The extract is dried with calcium chloride, the solvent distilled off and the residual 6-[ethyl(phenylmethyl)amino]-2methyl-4-(4-methyl-1-piperazinyl)-5-nitropyridine-3-carboxylic acid, ethyl ester is used without further purification, yield of crude product: 40 g. (90%).

c. 5-Amino-6-ethylamino-2-methyl-4-(4-methyl-1-piperazinyl)pyridine-3-carboxylic acid ethyl ester 4.4 g. of 6-[ethyl(phenylmethyl)amino]-2-methyl-4-(4-methyl-1-piperazinyl)-5-nitropyridine-3-carboxylic acid, ethyl ester are hydrogenated according to the procedure in Example 1 d. 5-Amino-6-ethylamino-2-methyl-4-(4-methyl-1-piperazinyl)pyridine-3-carboxylic acid, ethyl ester is obtained, yield 78%, m.p. 73°–75° (ethyl acetate).

d. 3-Ethyl-5-methyl-7-(4-methyl-1-piperazinyl)-3H-imidazo[4,5 -b]pyridine-3-carboxylic acid, ethyl ester 3.2 g. of 5-amino-6-ethylamino-2-methyl-4-(4-methyl-1-piperazinyl)pyridine-3-carboxylic acid, ethyl ester (0.01 Mol.) are heated at reflux temperature with 20 ml. of orthoformic acid triethylester for 12 hours. After this time, the excess ortho ester is distilled off and the residue is recrystallized from ether, yield 2.9 g. (88%), m.p. 70°–72°.

According to the procedure of Example 3, the following additional compounds are synthesized: 3-Ethyl-5-methyl-7-(4-phenyl-1-piperazinyl)-3H-imidazo[4,5-b]-pyridine-6-carboxylic acid, ethyl ester, m.p. 128°–130° and 3-Ethyl-5-methyl-7-piperidinyl-3H-imidazo[4,5b]pyridine-6-carboxylic acid ethyl ester, m.p. 37°–39°.

EXAMPLE 4

7-Butylamino-3,5-dimethyl-3H-imidazo[4,5-b]pyridine-6-carboxylic acid, ethyl ester a. 4-Chloro-6-(1-methyl)hydrazino-2-methyl-5-nitropyridine-3-carboxylic acid, ethyl ester 27.9 g. of 4,6-dichloro-2-methyl-5-nitropyridine-3-carboxylic acid, ethyl ester (0.1 Mol.) are dissolved in about 100 ml. of methanol. At 50°, 9.2 g. of methylhydrazine are dropped in and the mixture is stirred for 30 minutes. On cooling, 4-chloro-6-(1-methyl)hydrazino-2-methyl-5-nitropyridine-3-carboxylic acid, ethyl ester precipitates, yield: 18 g. (62.2%), m.p. 159°–161° (methanol).

b. 5-Amino-6-(methyl)amino-4-chloro-2-methylpyridine-3-carboxylic acid, ethyl ester 5.8 g. of 4-chloro-6-(1-methyl)hydrazino-2-methyl-5-nitropyridine-3-carboxylic acid ethyl ester is hydrogenated in 100 ml. of butanol with Raney nickel catalyst at 3 atm. of hydrogen pressure and 90°. When the hydrogen absorption ceases, the catalyst is filtered off and the solvent is removed in vacuo. Distillation of the residue yields 22 g. of 5-amino-6-(methyl)amino-4-chloro-2-methylpyridine-3-carboxylic acid, ethyl ester (91%), b.p.$_{0.05}$ 200°–210°.

c. 7-Chloro-3,5-dimethyl-3H-imidazo[4,5-b]pyridine-5-carboxylic acid, ethyl ester 2.4 of 5-amino-6-(methyl)amino-4-chloro-2-methyl-pyridine-3-carboxylic acid ethyl ester (0.01 Mol.) and 10 ml. of orthoformic acid triethylester are refluxed for 12 hours. After the excess orthoester is removed, the residue is recrystallized from ethyl acetate, m.p. 56°–58°, yield 2.2 g. (88%).

d. 7-Butylamino-3,5-dimethyl-3H-imidazo[4,5-b]pyridine-6-carboxylic acid ethyl ester 2.5 g. of 7-chloro-3,5-dimethyl-3H-imidazo[4,5-b]pyridine-6-carboxylic acid ethyl ester is refluxed for 10 minutes with 10 ml. of butylamine. The excess butylamine is removed and the residue dissolved in ether. The mixture is filtered and cooled. The 7-butylamino-3,5-dimethyl-3H-imidazo[4,5-b]pyridine-6-carboxylic acid ethyl ester precipitates and is recrystallized from petroleum ether, yield 78%, m.p. 62°–63°.

EXAMPLE 5

7-Butylamino-2-hydroxy-5-methyl-3H-imidazo[4,5-b]pyridine-6-carboxylic acid, ethyl ester a. 6-Amino-4-butylamino-2-methyl-5-nitropyridine-3-carboxylic acid, ethyl ester 177.9 g. of 4-butylamino-6-chloro-2-methyl-5-nitronicotinic acid ethyl ester (0.5 Mol.) and 500 ml. of methanol are heated in an autoclave together with 300 ml. of aqueous ammonia (30%) at about 60° for 10 hours. After this time, the solvent is distilled off and the residual 6-amino-4-butylamino-2-methyl-5-nitropyridine-3-carboxylic acid ethyl ester is recrystallized from methanol, yield: 135 g., m.p. 98°–99°.

b. 5,6-Diamino-4-butylamino-2-methylpyridine-3-carboxylic acid, ethyl ester 29.6 g. of 6-amino-4-butylamino-2-methyl-5-nitropyridine-3-carboxylic acid ethyl ester are dissolved in 150 ml. of acetic acid. The solution is heated at reflux temperature. Zinc is added carefully until the mixture is colorless (about 20 g.). Heating is continued for an additional 10 minutes. The mixture is then evaporated to dryness and about 100 ml. of water are added. The solution is then neutralized with aqueous ammonia and extracted three times with 100 ml. portions of ether. The ether extracts are combined, dried with calcium chloride and the solvent is evaporated. The oily residue of 5,6-diamino-4-butylamino-2-methylnicotinic acid, ethyl ester crystallizes from methanol, yield: 21 g. (79%), m.p. 82°–83° (methanol/H$_2$O).

c. 6-Amino-4-butylamino-5-[(ethoxycarbonyl)amino]-2-methyl-3-pyridine-3-carboxylic acid, ethyl ester 26.6 g. of 5,6-diamino-4-butylamino-2-methylpyridine-3-carboxylic acid, ethyl ester (0.1 Mol.) are dissolved in 100 ml. of methanol. 12 g. of triethylamine are added and 10.8 g. of chloroformic acid ethyl ester are added dropwise with stirring. After the addition is completed, 50 ml. of water is added and the precipitate is filtered off, yield: 25.3 g. (83%) of 6-amino-4-butylamino-5-[(ethoxycarbonyl)amino]-2-methyl-3-pyridine-3-carboxylic acid, ethyl ester, m.p. 172°–173° (ethanol).

d. 7-Butylamino-2-hydroxy-5-methyl-3H-imidazo[4,5-b]pyridine-6-carboxylic acid, ethyl ester 3.3 g. of 6-amino-4-butylamino-5[(ethoxycarbonyl)amino]-2-methyl-3-pyridine-3-carboxylic acid ethyl ester (0.01 Mol.) are heated at 220° for 5 minutes. After this time, the compound is cooled and the residue recrystallized from ethanol, to obtain 7-butylamino-2-hydroxy-5-methyl-3H-imidazo[4,5-b]pyridine-6-carboxylic acid, ethyl ester, yield: 2.2 g. (76%), m.p. 249°–252°.

The following compounds are prepared by the procedure of the foregoing examples:

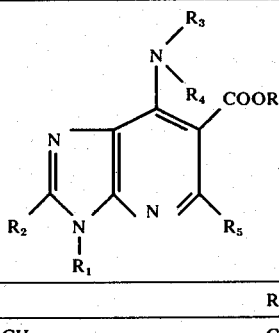

| Ex. | $R_1$ | $R_2$ | $R_3$ | $R_4$ | $R_5$ | R |
|---|---|---|---|---|---|---|
| 6 | $CH_3-CH_2$ | $CH_3$ | $CH_3-CH_2$ | $CH_3-CH_2$ | $CH_3$(HCl salt) | $C_2H_5$ |
| 7 | $CH_3-CH_2$ | H | $-CH_2-CH_2-\underset{\underset{CH_3}{\vert}}{N}-CH_2-CH_2-CH_2-$ | | H | $C_2H_5$ |
| 8 | $CH_3-CH_2$ | H | $-(CH_2)_3N(C_2H_5)_2$ | H | H | H |
| 9 | H | H | $-CH_2-CH_2-CH_2-CH_2-CH_2-$ | | $CH_3$(acetate salt) | $C_2H_5$ |
| 10 | $CH_3-CH_2$ | H | $CH_3-CH_2$ | $CH_3-CH_2$ | $C_2H_5$ | $CH_3$ |
| 11 | H | $C_2H_5$ | $-(CH_2)_2N(C_2H_5)_2$ | $CH_3$ | $CH_3$ | $C_2H_5$ |
| 12 | $CH_3-CH_2$ | $CH_3$ | H | H | $CH_3$ | $C_2H_5$ |
| 13 | $CH_3-CH_2$ | H | $-\underset{\underset{CH_3}{\vert}}{C}=CH-\underset{\underset{CH_3}{\vert}}{C}=N-$ | | $CH_3$ | $C_2H_5$ |
| 14 | $CH_3-CH_2$ | $CH_3$ | $-CH_2-CH_2-\underset{\underset{C_2H_5}{\vert}}{CH}-CH_2-CH_2-$ | | H | H |
| 15 | $CH_3-CH_2$ | $CH_3$ | $-CH_2-CH_2-CH_2-CH_2-$ | | $CH_3-$ | $C_2H_5$ |
| 16 | $CH_3-CH_2$ | H | $-CH_2-CH_2-\underset{\underset{CH_2-CH_2-OH}{\vert}}{N}-CH_2-CH_2-$ | | $CH_3-$ | $C_2H_5$ |
| 17 | $CH_3-CH_2$ | H | H | H | $C_3H_7$ | H |
| 18 | $CH_3$ | H | $-(CH_2)_3CH_3$ | H | $C_4H_9$ | $C_2H_5$ |
| 19 | $CH_3$ | H | $-(CH_2)_3CH_3$ | H | ⟨phenyl⟩ | H |
| 20 | $CH_3-CH_2$ | H | $-(CH_2)_3CH_3$ | H | $CH_3-$⟨phenyl⟩ | H |
| 21 | $CH_3-CH_2$ | H | $-CH=\underset{\underset{CH_3}{\vert}}{C}-C=\underset{\underset{CH_3}{\vert}}{C}-NH-$ | | $CH_3$ | $C_2H_5$ |
| 22 | ⟨phenyl⟩$-CH_2$ | H | $-(CH_2)_3CH_3$ | H | H | $C_2H_5$ |
| 23 | $CH_3-CH_2$ | H | ⟨phenyl-$CF_3$⟩ | H | $CH_3$ | $C_2H_5$ |
| 24 | $CH_3-CH_2$ | H | ⟨phenyl-$CF_3$⟩ | H | H | H |
| 25 | $CH_3-CH_2$ | $C_3H_7$ | $-CH_2-CH(CH_3)_2$ | H | $C_6H_5$ | $C_2H_5$ |

-continued

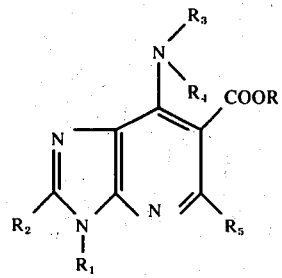

| Ex. | R₁ | R₂ | R₃ | R₄ | R₅ | R |
|---|---|---|---|---|---|---|
| 26 | $CH_3-CH_2$ | OH | $-CH(CH_3)-CH_2-CH_3$ | H | H | $C_2H_5$ |
| 27 | $CH_3-CH_2$ | $C_2H_5$ | $-CH_2-C_6H_5$ | H | $CH_3$ | $C_2H_5$ |
| 28 | $CH_3-CH_2$ | H | $-CH_2-CH_2-C_6H_5$ | H | H | $C_2H_5$ |
| 29 | $CH_3-CH_2$ | $CH_3$ | $-(CH_2)_3CH_3$ | $C_2H_5$ | H (HBr salt) | $C_2H_5$ |
| 30 | $CH_3-CH_2$ | H | $-(CH_2)_2CH_3$ | $-(CH_2)_2CH_3$ | $CH_3$ | $C_2H_5$ |
| 31 | $CH_3-CH_2$ | $-C_2H_4-C_6H_5$ | $-CH(CH_3)_2$ | H | $CH_3$ | $C_2H_5$ |
| 32 | $CH_3-CH_2$ | H | $-(CH_2)_5CH_3$ | H | H | $C_2H_5$ |
| 33 | H | $CH_3$ | $-(CH_2)_3CH_3$ | H | $CH_3$ | H |
| 34 | $CH_3-CH_2$ | H | $-C(CH_3)_3$ | $C_2H_5$ | H | $C_2H_5$ |
| 35 | $CH_3-(CH_2)_3$ | H | $-(CH_2)_3CH_3$ | H | H | $C_4H_9$ |
| 36 | $CH_3-CH_2-$ | H | 2,3-dimethylphenyl | H | $CH_3$ | $C_2H_5$ |
| 37 | $CH_3-CH_2-$ | H | 2,3-dimethylphenyl | H | $C_2H_5$ | H |
| 38 | $CH_3-CH_2$ | H | 2-COOH-phenyl | H | $CH_3$ | $C_2H_5$ |
| 39 | $CH_3(CH_2)_3$ | $CH_3$ | $-(CH_2)_3CH_3$ | H | $C_6H_5$ | $C_2H_5$ |
| 40 | $C_6H_5$ | H | $-(CH_2)_3CH_3$ | H | $CH_3$ | $C_2H_5$ |
| 41 | $CH_3$ | H | $CH_3-SO_2-$ | K⁺ | H | $C_2H_5$ |
| 42 | $CH_3-CH_2-$ | H | $-CH_2-CH_2-NH-CH_2-CH_2-$ | | $CH_3$ | H |
| 43 | H | $CH_3$ | $-CH_2-NH-CH_2-CH_2-CH_2-$ | | H | $C_2H_5$ |
| 44 | $CH_3-CH_2$ | $CH_3$ | $-NH-CH_2-CH_2-CH_2-CH_2-$ | | $CH_3$ | $C_2H_5$ |
| 45 | $CH_3-CH_2-$ | H | $CH_3-(CH_2)_3-$ | $CH_3-$ | 4-Cl-phenyl | $CH_3-CH_2-$ |
| 46 | $CH_3-CH_2-$ | H | 4-Cl-C₆H₄-CO- | H | $CH_3$ | $CH_3-CH_2$ |
| 47 | $CH_3-CH_2-$ | H | 4-Cl-C₆H₄-CO- | $CH_3-(CH_2)_3-$ | H | $CH_3-CH_2-$ |
| 48 | $CH_3-CH_2-$ | $CH_3$ | 4-$CH_3$-C₆H₄-SO₂- | Na⁺ | $CH_3$ | $CH_3-CH_2$ |
| 49 | $CH_3-CH_2-$ | H | $CH_2=CH-CH_2-$ | H | $CH_3$ | $CH_3-CH_2-$ |

-continued

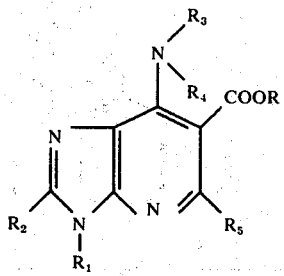

| Ex. | R₁ | R₂ | R₃ | R₄ | R₅ | R |
|---|---|---|---|---|---|---|
| 50 | CH₃—CH₂— | H | o-aminophenyl | H | H | CH₂—CH₃— |
| 51 | —(CH₂)—C₆H₅ | H | CH₃—(CH₂)₃— | H | CH₃ | CH₃—(CH₂)₆— |
| 52 | CH₃—CH₂—CH₂— | phenyl | CH₃—(CH₂)3— | H | CH₃ | CH₃—CH₃— |
| 53 | CH₃—CH₂— | CH₃ | —CH₂—CH₂—N(CH₃)—CH₂—CH₂— | | H | CH₂—CH₂ |
| 54 | H | H | CH₃CO— | H | CH₃ | H |
| 55 | CH₃—CH₂— | H | CH₃CO— | CH₃—CO— | H | CH₃—CH₂— |
| 56 | C₂H₅ | CH₃ | C₆H₅—CO— | H | CH₃ | CH₃—CH₂— |
| 57 | H | CH₃ | CH₃—(CH₂)₃— | H | | CH₃—CH₂— |
| 58 | 4-Cl-C₆H₄—CO— | CH₃ | CH₃—(CH₂)₃— | H | CH₃ | CH₃—CH₂— |
| 59 | H | CH₃ | CH₃—(CH₂)₃— | H | | H |
| 60 | H | H | CH₃—(CH₂)₃— | H | | CH₃—CH₂— |
| 61 | H | H | C₆H₅ | H | CH₃ | CH₃—CH₂— |
| 62 | CH₃CO— | H | CH₃—(CH₂)₃— | H | H | H |
| 63 | C₆H₅—CO— | CH₃ | C₂H₅ | C₂H₅ | H | CH₂—CH₂— |
| 64 | thienyl | H | CH₃(CH₂)₃ | H | H | CH₃—CH₂— |
| 65 | thienyl | CH₃ | C₂H₅ | C₂H₅ | CH₃ | H |
| 66 | CH₃CH₂CO— | H | CH₃—(CH₂)₅ | H | CH₃ | C₂H₅ |
| 67 | C₂H₅ | H | C₆H₅ | | H | C₂H₅ |

What is claimed is:
1. A compound of the formula

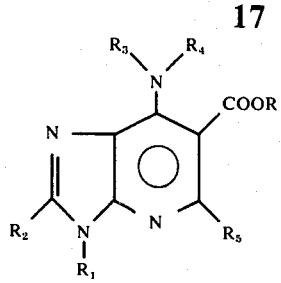

wherein

R is hydrogen or lower alkyl;

$R_1$ is hydrogen, lower alkyl, phenyl, phenyl-lower alkyl, cyclo-lower alkyl, lower alkanoyl, benzoyl or substituted benzoyl;

$R_2$ is hydrogen, lower alkyl, phenyl-lower alkyl or hydroxy;

$R_3$ and $R_4$ each is hydrogen, lower alkyl, lower alkenyl, lower alkanoyl, phenyl, substituted phenyl, phenyl-lower alkyl, di-lower alkylamino-lower alkyl, benzoyl, substituted benzoyl, lower alkanesulfonyl, benzenesulfonyl or substituted benzenesulfonyl; the substituents on said foregoing substituted radicals being lower alkyl, halogen, trifluoromethyl, amino or carboxy; or $R_3$ and $R_4$ together with the nitrogen form pyrrolidino;

$R_5$ is hydrogen, lower alkyl, phenyl or substituted phenyl, the substituents on said substituted phenyl being halogen, lower alkyl, amino, trifluoromethyl or carboxy; and physiologically acceptable salts thereof.

2. A compound as in claim 1 wherein R, $R_3$ and $R_4$ each is hydrogen or lower alkyl; $R_1$ is hydrogen, lower alkyl, phenyl, phenyl-lower alkyl, or lower alkanoyl; $R_2$ is hydrogen, lower alkyl or phenyl-lower alkyl; and $R_5$ is hydrogen, $C_1$–$C_3$ alkyl or phenyl.

3. A compound as in claim 1 wherein R, $R_3$ and $R_4$ each is hydrogen or $C_1$–$C_4$ alkyl; $R_1$ is hydrogen, $C_1$–$C_4$ alkyl, phenyl, benzyl, phenethyl, acetyl or propionyl; $R_2$ is hydrogen, hydroxy, $C_1$–$C_4$ alkyl, benzyl or phenethyl; and $R_5$ is hydrogen, methyl or ethyl.

4. A compound as in claim 1 wherein R and $R_1$ each is hydrogen or ethyl; $R_2$ is hydrogen, methyl or hydroxy; $R_3$ is hydrogen; $R_4$ is $C_1$–$C_4$ alkyl; and $R_5$ is methyl.

5. A compound as in claim 1 wherein $R_3$ is hydrogen and $R_4$ is lower alkyl.

6. A compound as in claim 1 wherein $R_3$ is hydrogen and $R_4$ is di(lower alkyl)amino-lower alkyl.

7. A compound as in claim 1 wherein R, $R_1$, $R_4$ and $R_5$ each is lower alkyl and $R_2$ and $R_3$ each is hydrogen.

8. A compound as in claim 7 wherein R is ethyl, $R_1$ and $R_5$ each is methyl and $R_4$ is butyl.

9. A compound as in claim 1 wherein R, $R_4$ and $R_5$ each is lower alkyl and $R_1$, $R_2$ and $R_3$ each is hydrogen.

10. A compound as in claim 1 wherein R, $R_1$, $R_2$, $R_4$ and $R_5$ each is lower alkyl and $R_3$ is hydrogen.

11. A compound as in claim 10 wherein R and $R_1$ each is ethyl, $R_2$ and $R_5$ each is methyl and $R_4$ is butyl.

12. A compound as in claim 1 wherein R, $R_4$ and $R_5$ each is lower alkyl and $R_1$ and $R_3$ each is hydrogen and $R_2$ is hydroxy.

13. A compound as in claim 12 wherein R is ethyl, $R_4$ is butyl and $R_5$ is methyl.

14. A compound as in claim 6 wherein R, $R_1$, $R_2$ and $R_5$ each is lower alkyl.

15. A compound as in claim 6 wherein R and $R_1$ each is ethyl, $R_2$ and $R_5$ each is methyl and $R_4$ is dimethylaminopropyl.

16. A compound as in claim 1 wherein R, $R_2$, $R_4$ and $R_5$ each is lower alkyl and $R_1$ and $R_3$ each is hydrogen.

17. A compound as in claim 16 wherein R is ethyl, $R_2$ and $R_5$ each is methyl and $R_4$ is butyl.

* * * * *